(12) United States Patent
Meltsner et al.

(10) Patent No.: US 9,155,908 B2
(45) Date of Patent: Oct. 13, 2015

(54) SIMULTANEOUS MULTI-MODALITY INVERSE OPTIMIZATION FOR RADIOTHERAPY TREATMENT PLANNING

(75) Inventors: Michael Meltsner, Fitchburg, WI (US); Ying Xiong, Naperville, IL (US); Michael Kaus, Madison, WI (US)

(73) Assignee: Koninklijke Philips N.V., Eindhoven (NL)

( * ) Notice: Subject to any disclaimer, the term of this patent is extended or adjusted under 35 U.S.C. 154(b) by 339 days.

(21) Appl. No.: 13/702,129

(22) PCT Filed: Apr. 27, 2011

(86) PCT No.: PCT/IB2011/051842
§ 371 (c)(1),
(2), (4) Date: Dec. 5, 2012

(87) PCT Pub. No.: WO2011/154853
PCT Pub. Date: Dec. 15, 2011

(65) Prior Publication Data
US 2013/0090549 A1    Apr. 11, 2013

Related U.S. Application Data

(60) Provisional application No. 61/353,672, filed on Jun. 11, 2010.

(51) Int. Cl.
*A61B 5/05* (2006.01)
*A61N 5/10* (2006.01)
(Continued)

(52) U.S. Cl.
CPC ............ *A61N 5/1031* (2013.01); *A61B 5/0073* (2013.01); *A61B 5/055* (2013.01);
(Continued)

(58) Field of Classification Search
CPC ...... A61N 5/1031; A61N 5/1042; A61N 5/10
USPC .................................. 600/407, 410, 424, 423
See application file for complete search history.

(56) References Cited

U.S. PATENT DOCUMENTS 6,735,277 B2    5/2004    McNutt et al.
6,882,702 B2    4/2005    Luo
(Continued)

FOREIGN PATENT DOCUMENTS

WO        03092789 A2    11/2003
WO    2005072825 A1     8/2005
WO    2009031073 A2     3/2009

OTHER PUBLICATIONS

Nill, S.; Development and application of a multi-modality inverse treatment planning system; 2001; Dissertation for Doctor of Natural Sciences—University of Heidelberg, Germany. http://archiv.ub.uni-heidelberg.de/volltextserver/volltexte/2001/1802/pdf/diss.pdf retrieved on Oct. 24, 2011.
Oelfke, U., et al.; Inverse Planning for Photon and Proton Beams; 2001; Medical Dosimetry; 26(2)113-124.

*Primary Examiner* — Joel Lamprecht

(57)    ABSTRACT

When performing multimodal radiotherapy planning, an optimizer (36) concurrently optimizes a combined treatment plan that employs an intensity modulated radiotherapy (IMRT) device (30) and an intensity modulated proton therapy (IMPT) that respectively generate a photon beam and an ion beam for treating a volume of interest (18) in a patient (34). A simulator (40) iteratively generates multiple variations of a simulation model (44) according to optimization parameters that are varied by the optimizer (36) until the simulation model (44) satisfies user-entered treatment objective criteria (48) (e.g., maximum dose, does placement, etc.)

24 Claims, 3 Drawing Sheets

(51) Int. Cl.
*G06F 19/00* (2011.01)
*A61B 5/00* (2006.01)
*A61B 5/055* (2006.01)

(52) U.S. Cl.
CPC ............ *A61B 5/4836* (2013.01); *A61N 5/103* (2013.01); *A61N 5/1039* (2013.01); *A61N 5/1042* (2013.01); *A61N 5/1078* (2013.01); *G06F 19/3437* (2013.01); *G06F 19/3481* (2013.01); *A61N 2005/1087* (2013.01)

(56) References Cited

U.S. PATENT DOCUMENTS

| | | |
|---|---|---|
| 2002/0046010 A1 | 4/2002 | Vessol et al. |
| 2003/0219098 A1 | 11/2003 | McNutt et al. |
| 2007/0034812 A1* | 2/2007 | Ma et al. .................. 250/492.21 |
| 2007/0201614 A1 | 8/2007 | Goldman et al. |
| 2009/0316858 A1 | 12/2009 | Nord et al. |

* cited by examiner

SIMULTANEOUS MULTI-MODALITY INVERSE OPTIMIZATION FOR RADIOTHERAPY TREATMENT PLANNING

CROSS REFERENCE TO RELATED APPLICATIONS

This application is a national filing of PCT application Serial No. PCT/IB2011/051842, filed Apr. 27, 2011, published as WO 2011/154853 A1 on Dec. 15, 2011, which claims the benefit of U.S. provisional application Ser. No. 61/353,672 filed Jun. 11, 2010, which is incorporated herein by reference.

The present application finds particular utility in multimodal radiotherapy planning optimization procedures and systems. However, it will be appreciated that the described technique(s) may also find application in other types of therapy planning systems, other therapy planning systems, and/or other medical applications.

Optimization algorithms for external beam radiotherapy have existed for some time. However, cancer treatment centers throughout the world are incorporating more types of radiation modalities into the planning process as they become available. For example, a treatment site may combine proton and photon based external beam therapies into one prescription for cancer patients. Such combination therapies utilize separate algorithms for optimizing the dose given to the patient for each type of modality. These algorithms inherently determine a sub-optimal solution because the optimization regimes are not inclusive of all treatment types simultaneously.

In traditional inverse planning algorithms, the software attempts to create a set of radiation beam shapes and weights to satisfy the user defined objectives. These objectives may include min, max, uniform, etc., dose to the target cancer site and/or surrounding organs. These algorithms utilize only one treatment modality at a time, with photons being the most widely used type. Since the inception and clinical use of inverse, intensity-modulated therapy, more cancer centers have gained access to different treatment modalities. These may include photon, electron, proton, ion therapy, etc.

Currently, there are radiation therapy devices which deliver photons of radiation and other radiation therapy devices which deliver ions, such as protons. Each has its own advantages and disadvantages. For example, ions can be focused to specific depths, have a higher tumor killing power, and can be accurately aimed. Photons have a wider distribution and are especially valuable for irradiating larger areas, such as a distribution of tumors, the peripheral area at the edges of tumors, and the like. Although there are dose optimization programs for each, such programs only optimize the dose of one of these modalities.

There is an unmet need in the art for systems and methods that facilitate using a single combined optimization technique for multimodal radiation therapy planning, and the like, thereby overcoming the deficiencies noted above.

In accordance with one aspect, a system that facilitates optimization of a multimodal radiation therapy plan employing both photon beam and ion beam radiation treatments includes an input graphical user interface (GUI) that includes a display on which is presented to the user information related to one or more radiation treatment plan simulation models. The system further includes an optimizer that concurrently optimizes dose delivery from a photon therapy device and an ion therapy device in one or more simulation models by iteratively adjusting a plurality of optimization parameters for each of the photon therapy device and the ion therapy device during simulation. Additionally the system includes a simulator that generates the one or more simulation models according to the optimization parameters.

In accordance with another aspect, a method of optimizing a multimodal radiation therapy plan employing both photon beam and ion beam radiation treatments includes concurrently optimizing dose delivery from a photon therapy device and an ion therapy device in one or more simulation models by iteratively adjusting a plurality of optimization parameters for each of the photon therapy device and the ion therapy device during simulation. The method further includes generating the one or more simulation models according to the optimization parameters.

In accordance with another aspect, a system that facilitates concurrently optimizing multiple modes of a multimodal therapy treatment plan includes a first therapy device that generates a first beam for treating a volume of interest in a patient, and a second therapy device that generates a second beam for treating the volume of interest in the patient. The system further includes an optimizer that evaluates one or more radiation treatment objective criteria and adjusts one or more optimization parameters associated with the first and second beams to achieve the one or more radiation treatment objective criteria, and a simulator that generates a plurality of simulation models based on the adjusted optimization parameters. The optimizer identifies an optimal simulation model from the plurality of simulation models and provides the optimal model to a controller for execution using the first therapy device and the second therapy device.

One advantage is that radiation dose to the patient is minimized.

Another advantage resides in improved dose delivery accuracy.

Still further advantages of the subject innovation will be appreciated by those of ordinary skill in the art upon reading and understand the following detailed description.

The drawings are only for purposes of illustrating various aspects and are not to be construed as limiting.

The described innovation relates to a single optimization routine which optimizes both photon and ion, e.g., proton delivery. This facilitates tumor treatment with a combination of photons and ions. The optimization is an iterative process in which the various factors or parameters for optimizing photon dose and the various factors or parameters for optimizing ion dose are combined with the differences in characteristics and advantages of photon versus ion treatment. In this manner, an optimal, combined photon and ion treatment plan is generated in a single optimization process.

Figure 1:
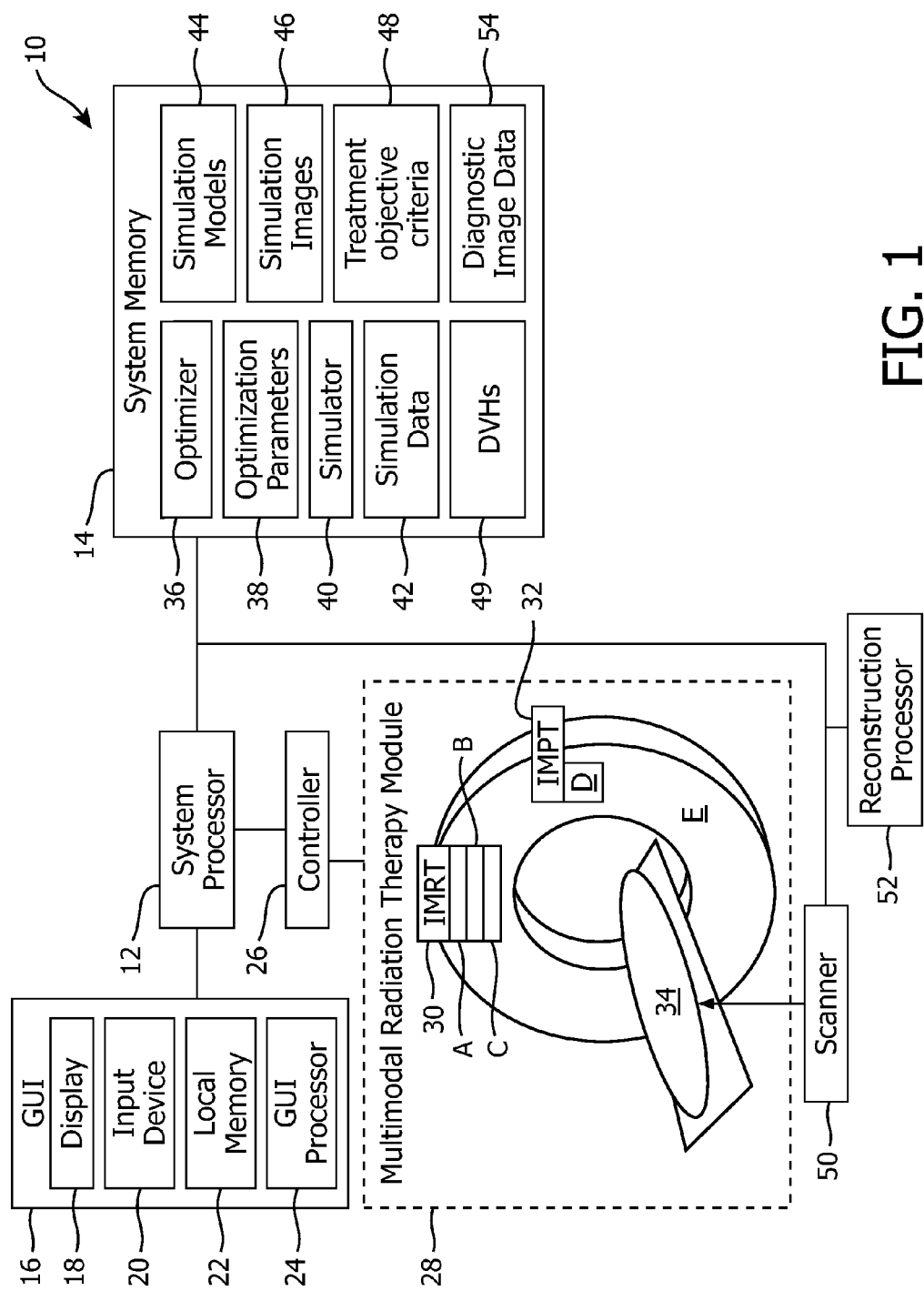
FIG. 1 illustrates a system that facilitates multimodal radiotherapy optimization, in accordance with various aspects described herein.

FIG. 1 illustrates a system 10 that facilitates multimodal radiotherapy optimization, in accordance with various aspects described herein. In contrast to conventional optimization techniques, in which if a user desires to combine therapies he/she would historically have to create a plan based on each modality separately and is forced to optimize or plan for only one delivery option at a time, the system of FIG. 1 facilitates simultaneous optimization whereby the user can incorporate multiple radiotherapy modalities into one combined optimization problem. Thus, the dose delivered by one type of source can be optimized and included during the optimization of the other.

Accordingly, the system 10 includes a system processor 12 that executes, and a system memory 14 that stores, computer executable instructions for carrying out the various functions and/or methods described herein. A control program is stored on a non-transient computer-readable medium or memory 14, such as a disk, hard drive, or the like. Other common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 12 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

The system processor 12 is coupled to a graphical user interface (GUI) 16 (e.g., a workstation or the like), which includes a display 18 on which information is presented to a user, an input device 20 (e.g., a keyboard, mouse, stylus, microphone, etc.) by which the user enters information into the system, a local memory 22 (e.g., for buffering data presented to the user via the display), and a GUI processor 24 (e.g., for displaying information to the user via the display, receiving input via the input device, communicating with the system processor, etc.).

The system processor 12 is also coupled to a controller 26 that controls a multimodal radiation therapy module 28 that comprises an intensity modulated radiotherapy (IMRT) device 30 for photon therapy, and an intensity modulated proton therapy (IMPT) device 32 for proton or ion therapy (e.g., hydrogen ions, carbon ions, etc.). The IMRT in one embodiment includes an x-ray tube A with a multi-leaf collimator B and a shutter C that is mounted on a rotatable gantry to irradiate the patient 34 from selected angles. The IMPT in one embodiment includes a linear accelerator D that is mounted to the rotatable gantry to irradiate the patient from selected angles. In one embodiment, the IMRT and the IMPT share a common gantry E. This enables the IMRT and the IMPT treatments to be delivered concurrently, sequentially, or alternately. In another embodiment, the IMRT and IMPT are on separate gantries. The patient moves between the gantries for sequential or alternate treatment, while other embodiments are separate systems that take advantage of the combined planning and optimization as described herein. In another embodiment, the proton treatment is delivered via a "fixed" nozzle technique or the like.

It will be appreciated that although the herein-described systems and methods relate to intensity modulated photon and ion therapy devices, other optimization processes may be employed in conjunction with the various aspects and features presented herein. For instance, in one embodiment one or both of the ion and photon therapy devices may be volume-modulated (e.g., a volumetric modulated arc therapy, or VMAT, device).

The IMRT and IMPT are used to treat a patient 34 using a combined or dual radiation treatment plan. To this end, an optimizer module or algorithm 36 is stored in the system memory 14 and executed by the system processor 12 to optimize both IMRT and IMPT dose as a function of one or more optimization parameters 38. The optimization parameters may include without limitation beam delivery parameters, beam trajectory, dose delivery, distance to target volume within the patient, beam intensity, dose per unit of time, beam placement on the target, machine characteristics, dose calculation algorithms, contouring of the volume of interest and/or patient, etc.), etc.

In one embodiment, the optimizer 36 employs an inverse planning algorithm for intensity modulated radiotherapy, such as is described in U.S. Pat. No. 6,735,277 to McNutt et al. In another embodiment, the optimizer 36 employs an inverse planning algorithm for intensity modulated radiotherapy, such as is described in U.S. Pat. No. 6,882,702 to Luo et al. However, where the McNutt and Luo patents deal only with IMRT optimization, the optimizer 36 performs an inverse optimization that concurrently accounts for both photon dose using IMRT as well as proton or ion dose using IMPT. That is, the optimizer accounts for all variables and parameters associated with optimizing both an IMRT and an IMPT dose delivery, and does so concurrently during a single optimization event rather than separately optimizing the photon and ion therapies.

A simulator module or algorithm 40 is stored in the system memory and executed by the system processor to generate simulation data 42 according to the optimization parameters, and the simulation data is used to develop one or more simulation models 44 comprising a plurality of simulation images that can be viewed on the display 18 by a user. The optimizer iteratively adjusts one or more optimization parameters to adjust the simulations, until an optimal combination therapy is identified. The optimal combination therapy is determined as a function of whether the optimal simulation meets certain treatment objective criteria 48 (e.g., maximum does at target center, uniform dose throughout target, etc.) specified by the user (e.g., overall dose minimization to the patient and/or healthy tissue, time constraints, maximum dose delivery to the target, etc.). In another embodiment, the optimizer identifies predetermined treatment objective criteria, e.g. as a function of one or more patient parameters and/or information associated with the patient, the region of interest, etc. Additionally, dose volume histogram graphs (DVHs) 49 can also be generated by the system processor (e.g., by executing the simulator 40) over the whole patient as well as specific areas.

In one embodiment, the system 10 includes a CT or other diagnostic scanner 50 that scan the patient to acquire scan data of a region of interest or target in the patient. In another embodiment, the scanner 50 is a magnetic resonance imaging (MRI) device. The acquired data is reconstructed by a reconstruction processor 52 into diagnostic image data 54 which are stored in the system memory 14. The diagnostic image data is segmented to identify the location, size, shape, etc., of the target(s) such as tumors to be treated, as well as sensitive tissue to be avoided and dense tissue such as bone, which can adversely affect dose deliver, e.g., by absorbing radiation or ions before they reach the target. Based on the segmented CT image (or other diagnostic image), which identifies the target or region of interest, the user enters (or the system determines) treatment objective information 48 (e.g., minimum dose, maximum dose, dose permitted in a given region, etc.) and the optimizer 36 iteratively adjusts optimization parameters while the simulator simulates beam origination points, intensities, depths, shapes or cross-sections, coverage areas, etc., to generate treatment simulation models. Once an optimized simulation model (e.g., with minimal radiation dose) is identified, it is presented to the user via the display 18 for optional further adaptation and adjustment (e.g., via manual adjustment of the optimization parameters or the like).

According to an example, the optimizer module 36 adjusts coverage area, dose, delivery parameters, etc., for the IMRT device 30 and analogous parameters and beam penetration depth for the IMPT device 32 to meet treatment objective criteria using a trial and error approach. Given the user-specified treatment objectives, the optimizer identifies an optimal simulation model from among a plurality of simulation models generated during execution of the optimizer module 36.

For instance, the IMRT dose may be weighted against IMPT dose as a function the size, shape, and/or location of the target volume to be treated. In one embodiment, IMRT treatment is opted for by the optimizer in regions of the target where broad, but less effective coverage is desired, while IMPT treatment is opted for where more precise and more powerful coverage is desired. For example, the optimizer may suggest application of a proton or ion beam from the IMPT device to irradiate a tumor in the patient, along with application of a photon beam from the IMRT device to irradiate an expansion around the tumor. The IMRT also irradiates the tumor causing the IMPT dose to be adjusted accordingly. Penetration statistics of the IMPT beam indicate that it will partially treat portions of the expansion region causing the IMRT dose distribution to be adjusted.

According to another example, the user enters a total permissible radiation dose as a treatment objective criteria, and the optimizer determines a ratio of ion to photon radiation that will be employed in each region of the treated area by optimizing the photon treatment plan, subtracting the amount of photon radiation from the total or maximum permissible dose to determine a maximum ion radiation dose, and then optimizing ion treatment plan to conform to the maximum allowable ion dose. Since ion radiation treatment is typically more biologically harmful than photon treatment for the same dose, the proton dose may be weighted when calculating photon and ion components of the total dose (e.g., the ion dose may be multiplied by a factor of 1.1 or so and added to the photon dose to equal the total biologically equivalent dose).

It will be appreciated that each radiotherapy beam may represent a different modality or combination of modalities. The multimodal radiotherapy optimization algorithm 36 in one embodiment further incorporates the relative biological efficiency of the radiation type as well as uncertainties such as organ motion, setup error, and uncertainties in the image-to-density or image-to-stopping power conversion. The dose of each beam type is calculated and incorporated simultaneously during the optimization process. The treatment planning system 10 is thus able to compute radiation dose with multiple sources of radiation (e.g., photon, electron, brachytherapy, proton, etc.). Due to the unique nature of the software, the user is able to perform therapy optimization and simulations that cannot be done using conventional techniques.

Figure 2:
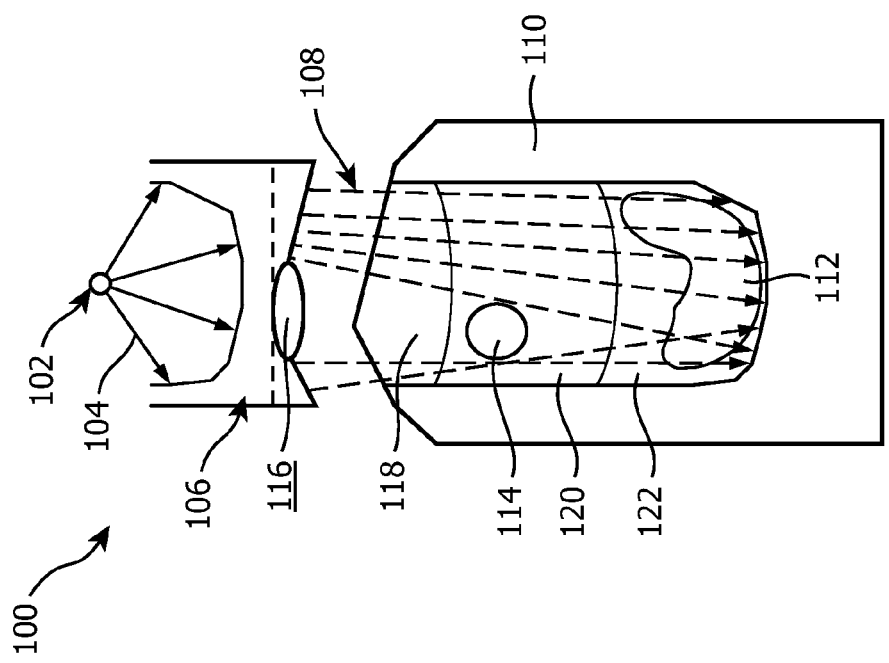
FIG. 2 illustrates a passive scattering proton delivery arrangement.

With continued reference to FIG. 1, FIG. 2 illustrates a passive scattering proton delivery arrangement 100. A proton dose is usually a summation of several layers of proton energies, all specific to the radiation device characteristics. A radiation source 102 emits proton beams 104 in a wide band, and the proton beams are passed through a compensator 106. Compensated proton beams 108 pass into a patient's body 110 to irradiate a tumor or other volume of interest 112. If there is a critical structure 114 (e.g., an organ, bone, or other tissue to be avoided), then a shield or the like 116 is positioned between the compensator and the patient to minimize radiation dose to the critical structure.

The proton beam is set to a predetermined depth, typically just below the bottom of the volume of interest 112. Due to the nature of the passive scattering delivery of the proton beams, a relatively lesser radiation dose is received in a region 118 of the patient near the surface of the patient. As the beams penetrate deeper into a region 120, radiation dose increases. In a region 122 toward the maximum depth of the proton beams, the radiation dose is maximal. However, because proton beams in a passive scattering approach traverse so much patient tissue, an undesirable high radiation dose may be delivered to the patient in order to achieve a desired minimum dose at the target or volume of interest. Therefore, it may be desirable to employ a more focused ion or proton beam. That is while the passive scattering approach can employ a compensator to compensate the beam for a shape a distal end of the radiated region, a shape of the entry contour on the patient, and for inhomogeneities in the tissue, it does not permit proximal conformity. Furthermore, scatter of the beams can lead to hot and cold spots (regions of high or low radiation).

Figure 3:
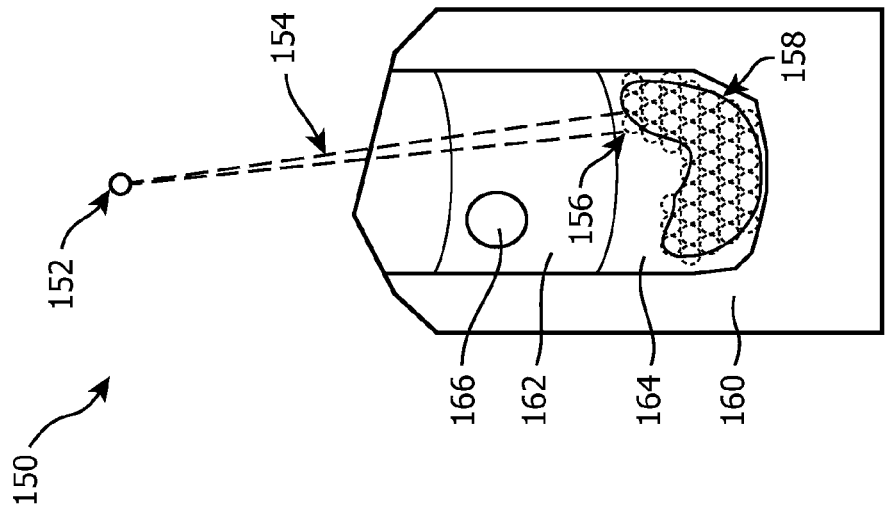
FIG. 3 illustrates a spot scanning radiation delivery arrangement that may be used for the IMPT and IMRT dose deliveries.

With continued reference to FIGS. 1 and 2, FIG. 3 illustrates a spot scanning radiation delivery arrangement 150 that may be used for the IMPT and IMRT dose deliveries. For IMPT dose delivery, the treatment planning system 10 performs an optimization, similar to and concurrently with IMRT for photon radiotherapy optimization. That is, the optimizer 36 combines IMRT and IMPT optimization into a single, more complex problem to be solved, and the simulator runs multiple simulations until an optimal solution is found. The optimal solution is determined as a function of user entered goals (e.g., minimal does to surrounding tissue, maximum does to target, maximum duration of treatment, etc.). For instance, if a tumor is positioned near an organ or other critical structure, then the user may specify a maximum radiation dose (e.g., 50 Gray) is allowed within 1 cm of the organ, while a higher dose is permitted outside of 1 cm. In this case, the optimizer may determine that the simulation model representing the optimal solution includes irradiating the tumor within the 1 cm boundary with a photon beam (or a combination of photon and ion beam doses), and irradiating the tumor outside of the boundary with an ion beam (or a combination of photon and ion beam delivery with a higher ion beam component than is applied inside the boundary).

In this arrangement of FIG. 3, a radiation source 152 delivers a focused ion beam 154 in the case of IMPT, also called a "pencil" beam, to a plurality of predetermined regions of interest 156 (e.g., voxels, spheres, etc.) defined throughout a volume of interest 158 in a patient 160. In another embodiment, the ion beam (and/or the photon beam) is modeled or simulated using a Monte Carlo simulation technique. The ion beam is redirected at intervals such that all of the volume of interest is irradiated, one zone at a time. The region 162 closest to the surface of the patient receives less radiation that it would using a passive scattering technique, while the region 164 surrounding the volume of interest receives a sufficiently high radiation dose to destroy cancer cells in the volume of interest. Because the beam is focused, any critical structures 166 can be avoided. In this manner, compensation scatter is eliminated and proximal conformity is improved.

Photon beams can be focused or shaped to irradiate a selected path through the subject. By irradiating the target from different directions, the cumulative dose delivered to the target is relatively high and the dose delivered to other tissues is relatively low.

In one embodiment, an IMPT dose of a predetermined magnitude is delivered to internal regions of interest, and an IMPT dose of a lesser magnitude is delivered to surface regions of interest and followed or preceded by IMRT doses through the target and closely adjacent tissue.

In another embodiment the optimizer 36 of FIG. 1 is executed to concurrently optimize IMRT and IMPT dose, delivery duration, beam depth, beam width or cross section, beam target(s) (e.g., regions of interest 156 to be targeted by one or both of the IMRT and IMPT beams), etc., according to radiation therapy goals input by the user. For instance, the optimizer 36 attempts to adjust the weights and positions of the individual "spots" of dose (i.e., the regions of interest 156) to achieve the desired result that is input by the user.

For example, the user may want to define a uniform dose to the target and define a maximum allowable dose to a normal piece of tissue. The optimizer 36 determines how and where the machine can place regions of interest (e.g., voxels) of dose within the patient, at what resolution a dose to those zones can be delivered in all directions, and a weight of each zone in order to achieve the desired result.

In another example, IMPT may be used for specific tissues such as the spine or prostate, since its depth is much easier to control that that of a photon beam.

IMRT may then be used for nearby or surrounding tissue where depth control is less important or where a lesser radiation dose is desired.

The concepts of IMRT and IMPT are similar, while the method in which respective photon and ion doses are delivered may not be. Thus, the optimization algorithms for dose computation and optimization for each type of delivery takes into account the inherent limitations and characteristics of each modality. The optimizer 36 is therefore considers all possible delivery constraints from both the photon and proton devices, and thereby represents a real world problem accurately. The user can, in real time, adjust the importance and the types and number of objectives they would like to satisfy. In some cases, the user may want to have different objectives assigned to the different modalities, for example if the user wants to preferentially irradiate one target with one modality more than another target. The user is able to visualize the results of the optimization process in real time via dose display (e.g., on the display 18).

The proton delivers more energy per centimeter of travel than the photon, and this energy loss is not constant over the whole range of the proton beam. Therefore, the optimizer accounts for this variance in relative biological effectiveness (RBE). The dose delivered from a proton beam can be less than a photon beam and still provide the same destructive result. For example, if it is determined that a tumor can be killed with 100 Gray worth of dose via photon, then the same result may be obtained using 90 Gray of dose from a proton beam.

In addition, proton beams are subject to a higher margin of error given uncertainty in the setup of the patient and the variance in tissue that may appear within the proton beam path. These factors are accounted for by the optimizer as well. Currently, IMPT is done using a spot scanning technique that scans the dose similar to how a cathode ray tube TV works. In one embodiment, the proton dose is modulated with the use of a multi leaf collimator or the like, similar to the way photons are modulated today, and the collimation is considered by the optimizer during combined optimization of the IMRT and IMPT dose deliveries.

Figure 4:
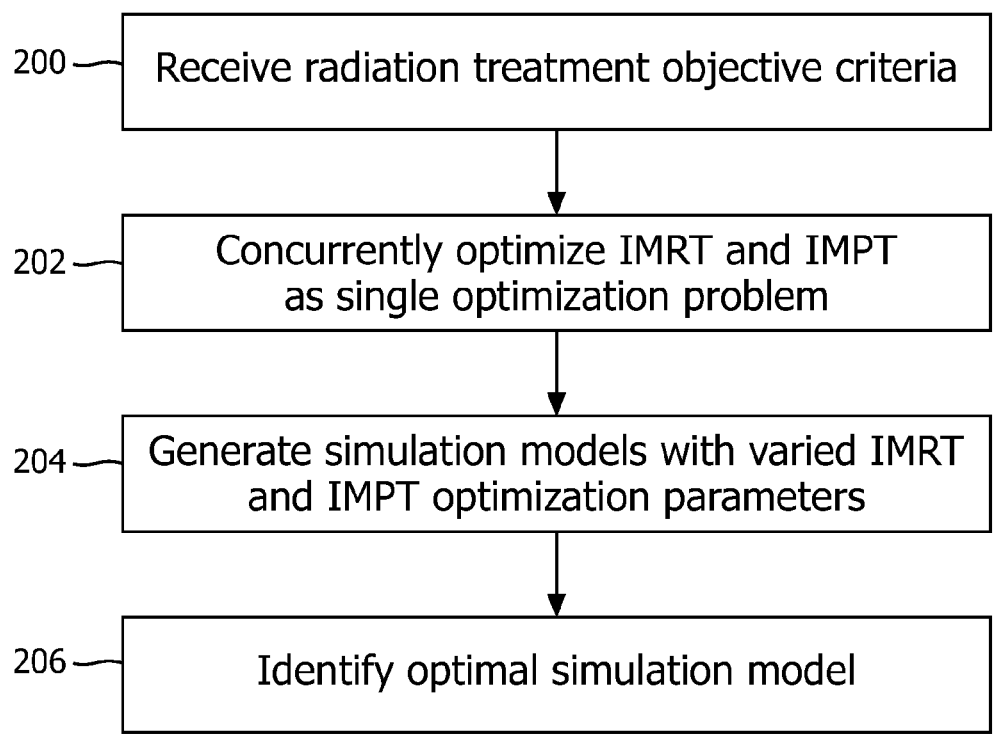
FIG. 4 illustrates a method of concurrently optimizing a multimodal radiotherapy plan for irradiating a volume of interest in a patient using IMRT and IMPT devices, in accordance with one or more aspects described herein.

FIG. 4 illustrates a method of concurrently optimizing a multimodal radiotherapy plan for irradiating a volume of interest in a patient using IMRT and IMPT devices, in accordance with one or more aspects described herein. At 200, radiation treatment objective criteria (e.g., max dose, minimum dose, etc.) are received. At 202, ion and photon radiation treatment plans are concurrently optimized by iteratively adjusting a plurality of optimization parameters (e.g., beam intensity, beam cross-section, beam depth, treatment duration, etc.) to achieve the specified objective criteria. In one embodiment, different objective criteria are assigned to the photon (IMRT) and proton (IMPT) radiation components of a combined treatment plan. At 204, a plurality of versions of the treatment plans is simulated. The simulated plans optionally are presented to a user on a display. At 206, an optimal combined treatment plan is simulated (e.g., as meeting the objective criteria with minimal dose, etc.).

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the inventions is now claimed to be:

1. A system that facilitates optimization of a multimodal radiation therapy plan employing both photon beam and ion beam radiation treatments, including:
    an input graphical user interface (GUI) that includes:
        a display on which is presented to the user information related to one or more radiation treatment plan simulation models;
    an optimizer configured to concurrently optimize dose delivery from a photon therapy device and an ion therapy device in one or more combined simulation models by iteratively adjusting a plurality of optimization parameters for both of the photon therapy device and the ion therapy device during simulation; and
    a simulator configured to generate the one or more combined simulation models according to the optimization parameters;
    wherein the system is further configured to display on the display one or more optimized combined simulation models.

2. The system according to claim 1, wherein the optimizer identifies an optimal combined simulation model that satisfies predefined radiation treatment objective criteria.

3. The system according to claim 1, further including:
    a diagnostic scanner that acquires image data of a volume of interest in a patient to be treated using a combined photon and ion radiation treatment; and
    a reconstruction processor that reconstructs the acquired image data into one or more images that are used by the simulator to identify contours of the patient and the volume of interest to be treated.

4. The system according to claim 1, wherein the ion therapy device emits one of a hydrogen ion beam, a proton beam, a carbon ion beam, or other ion beam.

5. The system according to claim 1, wherein the optimal simulation model represents a combined photon and ion treatment that destroys the volume of interest with a minimum combined radiation dose outside the volume of interest relative to other simulation models.

6. The system according claim 1, wherein the optimal combined simulation model is presented to the user on the display.

7. The system according to claim 1, further comprising a system processor that generates one or more dose volume histogram graphs (DVHs) that are presented to the user on the display.

8. The system according to claim 1, wherein the photon beam and the ion beam are one of pencil beams and Monte Carlo-modeled beams, and wherein the one or more combined simulation models comprise a plurality of regions of interest that cover the entire volume of interest.

9. The system according to claim 1, wherein the optimization parameters include one or more of:
- beam trajectory;
- dose delivery;
- distance to the volume of interest;
- beam intensity;
- dose per unit of time;
- beam placement on or within the volume of interest;
- machine characteristics;
- biological efficiency; and
- contours of the volume of interest or patient.

10. The system according to claim 1, further including an input device via which a user inputs radiation treatment objective criteria for a radiation treatment plan.

11. The system according to claim 1, wherein at least one of
- the photon therapy device is an intensity modulated radiotherapy (IMRT) device and the ion therapy device is a volume modulated arc therapy (VMAT) device;
- the photon therapy device is a VMAT device and the ion therapy device is an intensity modulated proton therapy (IMPT) device;
- the photon therapy device is an IMRT device and the ion therapy device is an IMPT device; and
- the photon therapy device is a VMAT device for photon therapy and the ion therapy device is a VMAT device for ion therapy.

12. The system according to claim 1, wherein the optimizer identifies an optimal combined simulation model from the one or more combined simulation models and provides the identified optimal combined model to a controller for execution using the first therapy device and the second therapy device.

13. A method of optimizing a multimodal radiation therapy plan employing both photon beam and ion beam radiation treatments, including:
- concurrently optimizing dose delivery from a photon therapy device and an ion therapy device in one or more combined simulation models by iteratively adjusting a plurality of optimization parameters for both of the photon therapy device and the ion therapy device during simulation; and
- generating the one or more combined simulation models according to the optimization parameters by simulating a proton or ion beam;
- displaying one or more optimized combined simulation models.

14. The method according to claim 13, further including:
identifying an optimal simulation model that satisfies predefined radiation treatment objective criteria.

15. The method according to claim 13, further including:
- acquiring image data, via at least one of a tomographic scanner and a magnetic resonance scanner, of a volume of interest in a patient to be treated using a combined photon and ion radiation treatment; and
- reconstructing the acquired image data into one or more volume images that are employed during generation of the simulation models to identify contours of the patient and the volume of interest to be treated.

16. The method according to claim 13, wherein the ion therapy device emits one of a hydrogen ion beam, a proton beam, a carbon ion beam, or other ion beam.

17. The method according to claim 13, wherein the optimal combined simulation model represents a combined photon and ion treatment that irradiates the volume of interest with a minimum combined radiation dose to tissue outside the volume of interest relative to other simulation models.

18. The method according to claim 13, further comprising generating one or more dose volume histogram graphs (DVHs) that are presented to the user on the display.

19. The method according to claim 13, wherein the one or more combined simulation models comprise a plurality of regions of interest that cover the entire volume of interest.

20. The method according to claim 13, wherein the optimization parameters include one or more of:
- beam trajectory;
- dose delivery;
- distance to the volume of interest;
- beam intensity;
- dose per unit of time;
- beam placement on or within the volume of interest;
- machine characteristics;
- biological efficiency; and
- contours of the volume of interest or patient.

21. A processor that configured to execute computer-executable instructions for performing the method of claim 13.

22. A non-transitory computer-readable medium that carries computer instructions that control a processor to perform the method of claim 13.

23. The method according to claim 14, further comprising receiving user input that describes the predefined radiation treatment objective criteria for a radiation treatment plan.

24. The method according to claim 13, wherein at least one of:
- the photon therapy device is an intensity modulated radiotherapy (IMRT) device and the ion therapy device is a volume modulated arc therapy (VMAT) device for ion therapy;
- the photon therapy device is a VMAT device for photon therapy and the ion therapy device is an intensity modulated proton therapy (IMPT) device;
- the photon therapy device is an IMRT device and the ion therapy device is an IMPT device; and
- the photon therapy device is a VMAT device for photon therapy and the ion therapy device is a VMAT device for ion therapy.

* * * * *